United States Patent
Runge et al.

(10) Patent No.: US 7,037,708 B1
(45) Date of Patent: May 2, 2006

(54) DRIED MICROORGANISM CULTURES AND METHOD FOR PRODUCING SAME

(75) Inventors: Frank Runge, Maxdorf (DE); Bryan Cooper, Mannheim (DE); Ulrich Bröckel, Freinsheim (DE); Robert Heinz, Ludwigshafen (DE); Hans-Peter Harz, Dudenhofen (DE); Ulrich Eidelsburger, Hessheim (DE); Bruno Käsler, Ludwigshafen (DE); Thomas Keller, Lautersheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/673,136

(22) PCT Filed: Apr. 29, 1999

(86) PCT No.: PCT/EP99/02925

§ 371 (c)(1),
(2), (4) Date: Oct. 11, 2000

(87) PCT Pub. No.: WO99/57242

PCT Pub. Date: Nov. 11, 1999

(30) Foreign Application Priority Data

Apr. 30, 1998 (DE) .......................... 198 19 475

(51) Int. Cl.
*C12N 1/20* (2006.01)

(52) U.S. Cl. ................ 435/243; 435/252.1; 435/252.9; 435/260; 424/93.4; 426/61; 426/471

(58) Field of Classification Search .............. 435/252.1, 435/252.9, 243, 266; 424/93.4; 426/61, 471
See application file for complete search history.

(56) References Cited

U.S. PATENT DOCUMENTS

| 3,407,072 | A | 10/1968 | Aizaea et al. ................... 99/96 |
| 3,536,498 | A | 10/1970 | Ano et al. ..................... 99/96 |
| 3,677,897 | A | 7/1972 | Jeffreys ...................... 195/55 |
| 3,897,307 | A | 7/1975 | Porubcan et al. ............. 195/59 |
| 3,988,440 | A | 10/1976 | Bogdanov ................... 424/115 |
| 5,928,469 | A | 7/1999 | Franks et al. ................. 159/48 |
| 6,010,725 | A | 1/2000 | Meister et al. ................ 426/61 |

FOREIGN PATENT DOCUMENTS

| EP | 131 114 | 1/1985 |
| EP | 202 409 | 11/1986 |
| GB | 1073030 | 6/1967 |
| GB | 2016043 | 9/1979 |
| JP | 69-67989 | 3/1973 |
| JP | 95 0577186 | 6/1995 |
| SU | 724 113 | 3/1980 |
| SU | 129 2706 | 2/1987 |
| SU | 161 6990 | 12/1990 |
| WO | WO 88/06181 | 8/1988 |

OTHER PUBLICATIONS

Stadhouders et al. "Preservation of Starters and Mass Production of Starter Bacteria" Neth. Milk Dairy J. vol. 32 (1969) pp. 182–199.

*Primary Examiner*—Leon B. Lankford, Jr.
(74) *Attorney, Agent, or Firm*—Keil & Weinkauf

(57) ABSTRACT

Dry microorganism cultures comprising at least one microorganism species in carrier-bound form are present in the form of particles which a) have a particle size of at least about 0.1 mm and b) are compressed; processes for preparing dry microorganism cultures and their use for preparing foodstuffs and feedstuffs are also claimed.

20 Claims, 1 Drawing Sheet

DRIED MICROORGANISM CULTURES AND METHOD FOR PRODUCING SAME

Figure 1:
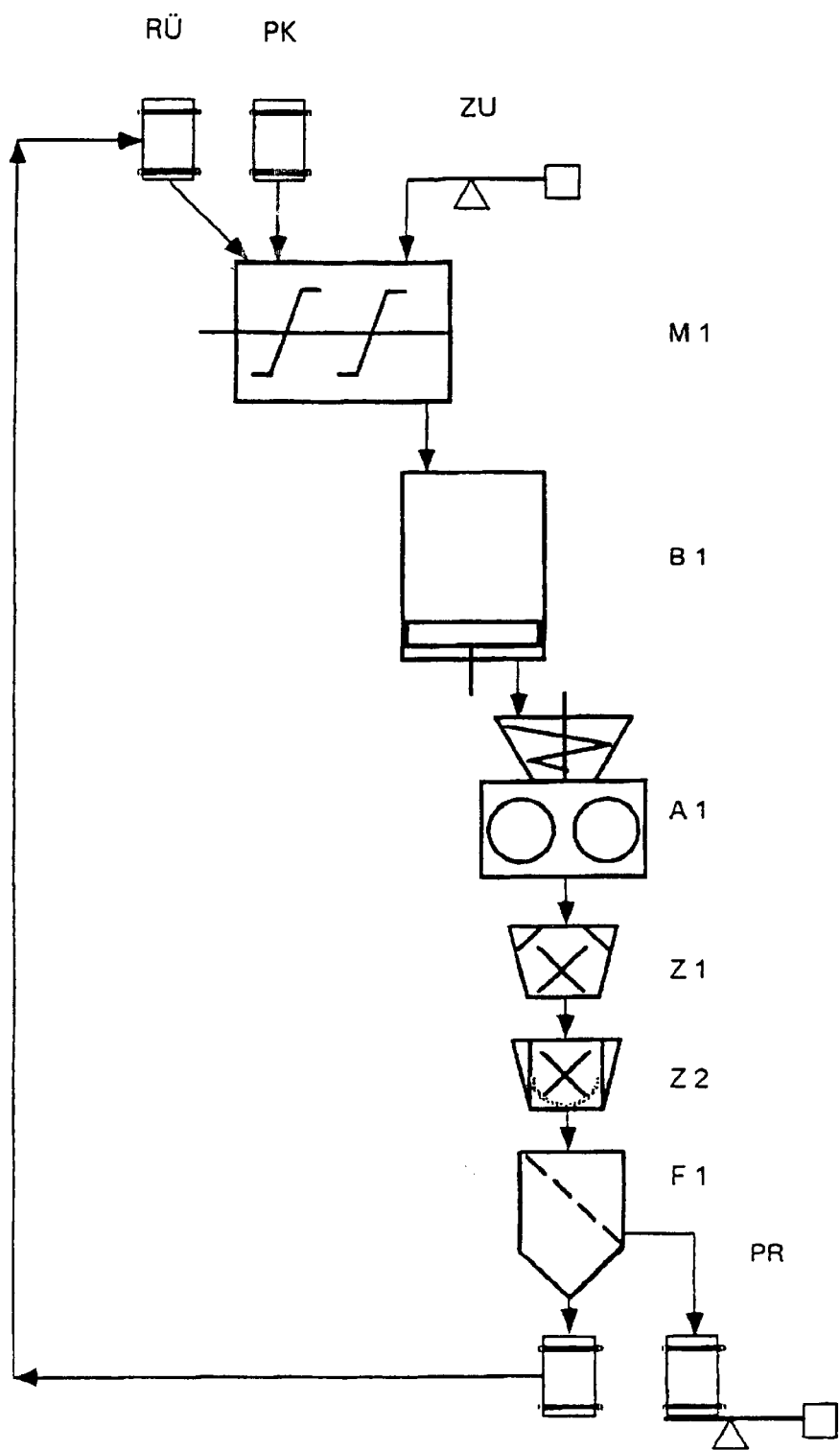

The present invention relates to novel dry microorganism cultures which can be used in particular to prepare foodstuffs and feedstuffs, and to processes for preparing dry microorganism cultures.

A main area of application of microorganisms, such as bacteria and yeasts, is preparing foodstuffs and feedstuffs. Thus, for example, lactic acid bacteria, such as those of the genus Streptococcus sp. or Lactobacillus sp. are used in the preparation of milk products, such as sour cream, buttermilk, yogurt, kefir, coumis, curd cheese and in the preparation of sourdough and for preserving uncooked sausage, such as salami. Lactic acid bacteria, such as those of the genus Lactobacillus sp., for instance, are also used in the production of feeds., such as silage.

The microorganism preparations required for preparing foodstuffs and feedstuffs are usually used in the form of starter cultures. These are generally not freshly prepared liquid cultures, but either cultures usually frozen in liquid nitrogen or dry preparations. Dry preparations are usually preferred, since their transport and storage is technically less complex in comparison with frozen preparations.

Very varied types of dry preparations of microorganism cultures are known from the prior art. Thus, for example, EP-A-0 131 114 describes a Lactobacillus preparation where a bacterial cell suspension is applied to a pulverulent or granulated carrier composition and dried. However, to store the preparation it is necessary to package this in an oxygen-free protective gas atmosphere. DD 840493952 proposes freeze-drying strains of cultured microorganisms for producing starter cultures, packaging them in film and storing them at 279 to 288 Kelvin. JP-A-06/217713 describes the production of special Lactobacillus starter cultures by spray-drying. EP-A-0 202 409 proposes subjecting dry cultures to a wet granulation, processing the granules to form spherical particles and then drying them. In addition, proposals are made in a number of publications to provide coated dry bacterial preparations (cf. U.S. Pat. No. 3,677,897 for example).

A number of different processes are described in the prior art to produce dry microorganism preparations. In addition to the freeze-drying and fluidized-bed drying processes mentioned above, another alternative production method is spray-drying a microorganism suspension. Thus, for example, Stadhouders, J. et al., in Neth. Milk Dairy J. 23 (1969) 182 describes the spray-drying of lactic acid bacteria at 70° C., coupled with a post-drying step at 27° C. in vacuo. Apparently, preconditioned, i.e. predried, air is not used for the drying. Before the drying, a calcium hydroxide slurry is added to the material to be sprayed. The calcium lactate formed during the spray-drying is advantageous, inasmuch as it is said to have a lower hygroscopicity. In other spray-drying processes known from the prior art, bacterial suspensions to which the most varied types of carrier materials have been added in advance are sprayed. Thus, for example according to SU 724113, a bacterial suspension admixed with dried milk powder, molasses and sodium glutamate is sprayed. According to SU 1616990, a bacterial suspension admixed with the mineral palygorskite is spray-dried. WO-A-88/06181 describes the spray-drying of a bacterial suspension admixed with clay. JP-A-69/67989 describes the spray-drying of yeast cells or bacterial cells which are suspended in a neutral or slightly acidic solution which comprises proteins, carboxymethylcellulose, alginate or alginate ester, disaccharides or higher saccharides or polyhydric alcohols.

The dry microorganism preparations which are known to date from the prior art, in particular those preparations which are used for producing foodstuffs or feedstuffs, have at least one of the following disadvantages:

1) the content of viable microbes per unit weight of the dry material is very low owing to the production method, so that large volumes of the dry preparation must be used in the final application;
2) the storage stability is too low, so that the dry preparations must be used within a few weeks, if storage under technically complex conditions is impossible;
3) the dry preparations have a high dust content, which makes their processing more difficult;
4) the mechanical stability is very low, so that on mixing the preparation with mineral additives, a finely divided abraded material is formed and separation of the solid preparation can be observed;
5) the dissolution rate of the dry preparations is not satisfactory, so that the desired microbiological process for producing the foodstuff or feedstuff only begins slowly and unwanted microorganisms are given the possibility of multiplying, which can lead to considerable losses in quality.

The production processes known to date from the prior art, in particular the spray-drying processes described to date, are also unsatisfactory for at least one of the following reasons:

1) the processes are technically very complex;
2) the microorganism survival rate in drying is too low;
3) the moisture content of the dry product is too high.

A first object of the present invention is thus the provision of improved dry microorganism cultures which substantially no longer have the abovementioned deficiencies known from the prior art. In particular, starter cultures which are improved in comparison with the prior art are to be provided. The starter cultures according to the invention are especially to enable improved production of silage.

A second object of the present invention is the provision of improved processes for producing dry microorganism cultures. In particular, an improved process for spray-drying microorganism cultures should be provided which enables the production of dry preparations having a high content of viable microbes and high storage stability.

The above first object is achieved by providing a dry microorganism culture which comprises at least one microorganism species in carrier-bound form, wherein the culture is present in the form of particles which a) have a particle size of at least about 0.1 mm and
b) are compressed.

The particulate cultures according to the invention are virtually dust free on account of the chosen particle size. The dust content is preferably in the range from about 0.01 to 0.05% by weight, based on the total weight of the dry culture. This corresponds to a dust index in the range from about 1 to 12 determined gravimetrically by a Casella instrument.

The particles according to the invention furthermore have a compressed, i.e. compact, structure. This is preferably achieved in their production by a compression step which is explained in more detail below and has not been previously described for dry microorganism preparations. In this operation a preliminary product obtained, for example, by spray-drying, freeze-drying or fluidized-bed-drying (such as the powder concentrate which is obtainable by a spray-drying variant according to the invention and is described below), which usually has a significant dust content (e.g. a dust index from about 25 to 100), is mechanically compressed.

The compression can be performed, for example, by compacting the pulverulent preliminary product under the action of linear forces, e.g. in the range from about 5 to about 25 kN/cm, in particular from about 10 to about 15 kN/cm, in conventional compacting apparatuses, for example. However, the preliminary product can also be tabletted under the action of pressures in the range from about 50 to about 250 MPa, in particular in the range from about 80 to 200 MPa, such as from about 90 to about 160 MPa, for instance, in conventional tabletting presses, for example. Particular preference is given to compression by compacting. In addition, preference is given to compacting powder concentrates obtained according to the invention by spray-drying.

The provision of microorganism cultures of the type described above surprisingly results in the processing, in particular as starter cultures, being markedly simplified and, moreover, the mechanical stability of the particles and thus the danger of separation of starter culture preparations being markedly decreased. Surprisingly, it has also been found that the compression of the pulverulent preliminary product virtually does not impair product quality with respect to the number of viable microbes. Rather, owing to the high density achieved, the ingress of air and moisture into the dry preparations according to the invention is significantly decreased in such a manner that a considerable improvement in storage stability can be achieved.

Thus, for example, survival rates of 60% and above after storage for one year at room temperatures were achieved. Advantageous storage stability data of this type have not been described hitherto.

In particular, the compressed particles can comprise compacted broken material (i.e. material obtained by comminuting with or without classifying compacted product extrudates) having a diameter of from about 0.1 mm to about 2 mm, preferably from 0.3 to 1.25 mm. The diameter here is a value calculated from the total mass distribution of the compressed particles and corresponds to the diameter of spheres of equal mass. The edge length of the particles is in the range from about 0.1 to 2 mm, in particular from about 0.1 to 1.4 mm.

The compressed particles can, furthermore, be present as tablets of any desired shape, such as round, polygonal or oval, having a diameter of from about 2 to 50 mm and a ratio of diameter to thickness of from about 1:0.1 to about 10:1, in particular from about 1:1 to about 5:1.

According to a further preferred embodiment of the invention, the dry microorganism cultures comprise, as further component, an effervescence additive, comprising an acid component, such as an organic nonvolatile carboxylic acid, and a gas-forming component, such as a $CO_2$-forming component. Effervescence formulations of this type have the particular advantage of a surprisingly rapid dissolution after application of the starter culture. As a consequence of this rapid dissolution of the starter culture in its surrounding medium, rapid multiplication of the starter culture microorganisms is ensured, as a result of which losses in quality of the product to be produced using the starter culture can be avoided surprisingly well.

Preferably, the dry culture compressed according to the invention comprises, as carrier, at least one matrix material for embedding the microorganism cells with or without at least one other additive which stabilizes the cells.

The carrier used in the dry cultures according to the invention comprises at least one matrix component added as coformulant prior to the drying to usually freshly grown microorganisms, selected from mono-, oligo- and polysaccharides, polyols, polyethers, polymers, such as CMC or PVP, oligo- and polypeptides, from natural sources, such as milk, meat or cereals, derived substances or mixed substances, such as sweet whey powder, wheat semolina bran, peptone, alginates, mineral compounds, or mixtures of such matrix substances. In addition, additives having a stabilizing action can be added together with the matrix substance or later, for example antioxidants, such as α-tocopherol or ascorbic acid, or mixtures thereof. Furthermore, a stabilizing action can be exerted by other substances, which are selected from inorganic salts, such as alkali metal chlorides or alkaline earth metal chlorides, inorganic or organic buffers, such as alkali metal phosphate buffer, amino acids, such as aspartic acid or glutamic acid and the salts thereof, organic carboxylic acids, such as citric acid, organic nonvolatile solvents, such as DMSO, and other compounds, such as β-carotene and mixtures of these.

The microorganism cultures according to the invention preferably comprise viable microorganisms in a concentration of $10^8$ to $10^{12}$ cfu (colony forming units)/g of dry culture. The powder concentrates produced according to the invention comprise from about $5 \cdot 10^8$ to $1 \cdot 10^{12}$, preferably about $4 \cdot 10^{11}$ to $8 \cdot 10^{11}$ cfu/g. The compressed cultures according to the invention comprise from about $1 \cdot 10^{11}$ to $4 \cdot 10^{11}$, in particular about $3 \cdot 10^{11}$ cfu/g. Starter cultures for producing silage comprise from about 1 to $7 \cdot 10^{10}$, in particular about $3 \cdot 10^{10}$ cfu/g.

In this process the microorganisms can be derived from one microorganism species or a plurality. A particularly preferred species are lactic-acid-producing bacteria, such as those which are suitable for silage production, such as, for example, Lactobacillus plantarum.

For the purposes of the invention, silage comprises feed plant products which have been preserved by the action of microorganisms, for example those based on grass, clover, straw, corn plants, fodder beets, legumes, cereals, such as corn and wheat, and the like.

The second object of the present invention described above is surprisingly achieved by providing a spray-drying process for producing a dry microorganism culture, comprising at least one microorganism species in carrier-bound form, which comprises a) dissolving or suspending at least one substance suitable for forming a carrier in a liquid comprising at least one microorganism species, b) drying the resultant mixture in a spray-dryer, for the spray-drying use being made of a conditioned dried gas heated to a temperature in the range of above about 80° C., in particular from about 90 to about 135° C., preferably from about 100 to about 110° C., such as about 105° C., and c) removing the dried material from the spray-dryer, this dried material having an exit temperature of from about 40 to 85° C., in particular from about 45 to 75° C., preferably from about 50 to 65° C., such as about 55° C.

This spray-drying process according to the invention is also called carrier-bound spray-drying process below. The gas used for the drying is preferably a dried gas having a dew point of below +5° C. in particular having a dew point of from about −10 to about −50° C., such as conditioned compressed air or conditioned nitrogen. For example, compressed air having a dew point of about −25° C. and nitrogen having a dew point of about −40° C. can be used. A dew point of +5° C. is equivalent to roughly 5 g of water per m³ of air.

According to a preferred embodiment of the spray-drying process according to the invention, in a downstream further stage d), the dried material is subjected to a post-drying. The post-drying temperature is in the range of from about 15 to 50° C., such as from about 25 to 40° C. The post-drying is performed, for example, in a gas atmosphere or in vacuo; alternatively to this, there is also the possibility of mixing a desiccant homogeneously with the dry microorganism preparation obtained in accordance with stage c).

Because of its design, the spray-drying process according to the invention surprisingly permits microorganism suspensions to be dried at survival rates of up to 100%. Owing to the use of conditioned gas in the spray-drying as well as the optional post-drying step, surprisingly, dry preparations having an extremely low moisture content (of from about 2 to 3% by weight of water), corresponding to a water activity $a_w$ of from 0.03 to 0.15, are provided. This directly causes the microorganism cultures which have been spray-dried according to the invention, with or without post-drying, to have survival rates of up to 60% after storage for 1 year at ambient temperature and ambient air conditions.

Owing to the surprisingly high survival rate in the above-described spray-drying, the content of viable microorganisms is markedly high. The resultant spray-dried product is therefore also called powder concentrate and, to reduce the concentration of viable cells, can be further diluted, depending on the field of application. The powder concentrate is particularly suitable for preparing the above-described compressed particulate cultures according to the invention.

The present invention therefore also relates to a process for producing the above-described compressed microorganism cultures, which comprises i) producing a powder concentrate of the microorganism culture by carrier-bound spray-drying, carrier-bound freeze-drying or carrier-bound fluidized-bed drying, ii) with or without admixing the powder concentrate with one or more coformulants and iii) compressing this mixture by compacting or tabletting.

Preferably, in a further process step, the compressed mixture is broken, i.e. comminuted, and may be classified to give compressed granules of the desired size using a screen of suitable mesh width.

The present invention further relates to a process for producing a dry agglomerated microorganism culture, which comprises i) producing a powder concentrate of the microorganism culture by carrier-bound spray-drying, carrier-bound freeze-drying or carrier-bound fluidized-bed drying, ii) with or without admixing the powder concentrate with one or more coformulants and iii) compressing this mixture by agglomeration.

Carrier-bound means here the presence of at least one matrix material of the above-described type during drying.

According to a preferred embodiment of the above-described compacting process or tabletting process or agglomeration process, stage i) is carried out in particular in accordance with the above-described spray-drying process.

The product obtained by the above-described compression processes is, for the purposes of the present invention, also called compressed or compacted dry concentrate (in the cfu range from about $1·10^{10}$ to $1·10^{11}$) and can be marketed as such, e.g. as a concentrated starter culture.

The present invention further relates to the use of the compressed dry microorganism cultures according to the invention as starter cultures for producing foodstuffs, such as for the production of milk products, such as sour cream, buttermilk, yogurt, kefir, coumis, curd cheese, for producing sourdough, uncooked sausage, and for producing feedstuffs, such as silage. For this purpose, the culture, with or without dissolution, is mixed with the foodstuff substrate or feedstuff substrate. If the cell count in the starter culture should be too high, it may be diluted, e.g. by mixing with an inert solid, such as lime, in particular feed lime.

The present invention further relates to foodstuffs and feedstuffs which have been produced using the starter cultures according to the invention.

The present invention is described in more detail in the sections now following with reference to the accompanying figure.

FIG. 1 shows diagrammatically a possible way of producing, from powder concentrate, granules compacted in accordance with the invention.

USABLE MICROORGANISMS

The present invention is not restricted in principle to certain microorganism cultures. Rather, those skilled in the art recognize that the present invention is applicable to any microorganisms, in particular bacteria and yeasts, which can be converted to a dry microorganism preparation under the conditions specified in the present description. A suitable group of microorganisms which can be used according to the invention are the group of lactic-acid-producing bacteria. In particular, these are bacteria which are suitable for the homofermentative lactic acid fermentation, i.e. break down glucose to lactate via the fructose bisphosphate pathway. Typical representatives of this group are bacteria of the genera Lactobacillus sp., Streptococcus sp. and Pediococcus sp. Concrete examples of lactobacilli which may be mentioned are *Lactobacillus bulgaricus, Lactobacillus acidophilus, Lactobacillus helveticus, Lactobacillus bifidus, Lactobacillus casei, Lactobacillus lactis, Lactobacillus delbrueckii, Lactobacillus thermophilus, Lactobacillus fermentum, Lactobacillus brevis* and *Lactobacillus plantarum*. Examples of suitable streptococci are *Streptococcus lactis, Streptococcus cremoris, Streptococcus diacetilactis, Streptococcus thermophilus, Streptococcus pyrogenes, Streptococcus salivarius, Streptococcus faecalis, Streptococcus faecium*; and examples of suitable pediococci are *Pediococcus cerevisiae* and *Pediococcus acidilactici*.

Fermentation of the Microorganisms

To carry out the present invention, preferably, use is made of freshly prepared microorganism suspensions. The fermentation media or fermentation conditions optimum for each microorganism are either known from the prior art or can be determined in only a few routine experiments by the person skilled in the art who is entrusted with the culture of microorganisms.

However, usually, the fermentation is carried out in such a manner that starting from a liquid or semi-solid preliminary culture (culture volume from about 10 to 200 ml), freshly prepared sterile fermentation medium is inoculated under sterile conditions, where the volumetric ratio of preliminary culture to culture medium can be from about 1:50 to 1:200. Preferably, freshly grown preliminary cultures are used which are in a late phase of logarithmic growth. Depending on the microorganism being grown, they are cultured under specific optimized growth conditions (such as temperature and pH). Usually, the growth temperature is in the range from about 20 to 40° C., but, for example when thermophilic bacteria are being grown, markedly higher temperatures can be present. The fermentation batch is kept uniformly agitated, for example by moderate stirring or introducing air or nitrogen in order to prevent the development of temperature or substance gradients and to ensure continuous growth in this manner. After the growth phase is complete (determined for example by achieving a defined cell density or consumption of one of the added nutrients), the cell suspension can be used directly to produce the dry preparations according to the invention.

However, it is also possible to concentrate the resultant original cell suspension to increase the cell count. Suitable methods for this are, for example, centrifugation, ultrafiltration or thin-film evaporation. However, a centrifugation step is usually used to concentrate the cell suspension, which centrifugation step is preferably carried out at a decreased temperature, that is to say in the range from about 4 to 10° C.

Instead of the concentration, or in combination with it, there is also the possibility of subjecting the freshly cultured cell suspension to a washing step in order to remove culture constituents, such as metabolic products, which may have an adverse effect on the activity. In this case, the procedure usually adopted is that, preferably at from about 4 to 10° C., the original culture broth is first concentrated to give a suspension of high cell density and this is then taken up in a suitable buffer solution and diluted to the desired cell density. If necessary, the washing step can also be repeated a plurality of times. Solids contents which can be used according to the invention of cultures of microorganisms suitable for producing the dry preparations according to the invention are usually in the range from about 5 to 25% by weight, such as from about 10 to 20% by weight.

The microorganisms can be cultured by batch fermentation or continuously.

To further illustrate the invention, in the section below, a more detailed description is given of culturing a lactic acid bacterium, in particular Lactobacillus plantarum. This is a bacterium which is to be found in particular on intact and decomposing plants and is particularly suitable for producing silage feedstuffs.

A suitable fermentation medium comprises, per liter of medium, from about 40 to 60 g of glucose, from about 30 to 60 g of yeast extract and a cocktail of customary trace elements, such as magnesium, manganese and, optionally, iron. The pH of the fermentation medium is from about 6 to 7. The fermentation temperature is from about 33 to 38° C. The pH of the fermentation medium can be kept within the desired range by adding sterile sodium hydroxide solution. Growth is complete when glucose consumption or lactic acid synthesis can no longer be observed.

According to a lactobacillus fermentation variant which is suitable according to the invention, after about 80% or 90% of the growth is achieved, the fermentation medium temperature is increased to from about 42 to 46° C. until the added glucose is completely consumed. It has been found according to the invention that cultures produced in this manner are particularly stable in particular in the spray-drying, as a result of which high survival rates are achievable. Comparable growth variants are also conceivable with other microorganisms which can be used according to the invention.

After growth is complete, the fermentation batch is brought to the desired cell density. If desired, the cell suspension can be washed until it is virtually lactate free. The cell count of a microorganism suspension suitable according to the invention is usually in the range from about $1 \times 10^{10}$ to about $5 \times 10^{12}$ cfu/g of suspension.

Carrier Substances

The dry microorganism cultures prepared according to the invention, in addition to any nonvolatile constituents present from the respective fermentation batch, such as metabolic products, comprise at least one matrix material with or without other stabilizing substances. These coformulants are preferably selected from inorganic salts or buffers, at least one other compound which is selected from mono-, oligo- and polysaccharides, polyols, polyethers, amino acids, oligo- and polypeptides, milk-derived compounds, organic carboxylic acids, mineral compounds, organic carrier materials such as wheat semolina bran, alginates, DMSO, PVP (polyvinylpyrrolidone), CMC (carboxymethylcellulose), α-tocopherol, β-carotene and mixtures thereof.

Examples of suitable saccharide carrier components are sucrose, fructose, maltose, dextrose, lactose and maltodextrin. An example of a suitable polyol is glycerol. Examples of suitable amino acids are glutamic acid, aspartic acid and the salts thereof. An example of a suitable peptide carrier is peptone. An example of a milk-derived compound is, in addition to the abovementioned maltodextrin, also sweet whey powder. Suitable organic carboxylic acids are, for example, citric acid, malic acid and L-ascorbic acid. Examples of suitable mineral carriers are montmorillonite and palygorskite.

However, preferably, as carrier for the dry microorganism preparations according to the invention, use is made of mixtures of the abovementioned classes of substances. Mixtures of this type preferably comprise, as main component, a matrix material, such as one of the abovementioned saccharide components or, for example, sweet whey powder, with or without a minor content of at least one further component, such as a buffer component (for example citric acid) or an antioxidant (for example L-ascorbic acid or α-tocopherol). The addition of further stabilizing constituents, such as sodium glutamate and/or peptone, has likewise proved to be advantageous.

The matrix component is customarily used in carrier compositions usable according to the invention in about 5 to 30 times the amount of the other carrier constituents. Examples of particularly suitable carrier combinations are:
 a) sweet whey powder/citric acid/L-ascorbic acid (weight ratio about 40:1:1).
 b) maltodextrin/lactose/citric acid/L-ascorbic acid (weight ratio about 20:20:1:1), unsupplemented or supplemented by about 1.5 parts of β-carotene and 0.5 part of α-tocopherol per part of citric acid.
 c) maltodextrin/sodium glutamate/L-ascorbic acid (weight ratio about 10:1.5:1).
 d) lactose/glucose/peptone/citric acid (weight ratio about 6:6:1.2:1).

The carrier substances according to the invention can be added to the microorganism suspension either as solid or in dissolved form. However, preferably, a sterile solution of the carrier/carriers is prepared, this is cooled to a temperature of from 4 to 10° C. and this is mixed with the likewise cooled microorganism suspension with gentle stirring. To prepare a homogeneous suspension, the resultant mixture is stirred with further cooling for a period of from about 10 minutes to 1 hour.

Preparation of Dry Microorganism Preparations

The microorganism suspension containing the carrier added in the manner described above can then be dried in various ways. Suitable drying processes are in principle freeze drying, fluidized-bed drying and, preferably, spray-drying. For the purposes of the present invention, spray-drying also comprises modified spray-drying processes, such as spray-agglomeration or agglomerating spray-drying. The latter process is also known under the name FSD (fluidized spray-dryer) process.

Freeze-drying for preparing dry microorganism cultures according to the invention can be carried out, for example, on the basis of the freeze-drying process described in EP-A-0 259 739 or U.S. Pat. No. 3,897,307. The contents of these publications are hereby incorporated completely by reference.

A suitable fluidized-bed drying process is described, for example, in the dissertation by U. Kessler on the subject "Experimentelle Untersuchung und Modellierung der Überlebensrate von Milchsäurebakterien bei der thermischen Trocknung" [Experimental study and modeling of the survival rate of lactic acid bacteria during thermal drying], Technical University of Munich, 1993. The contents of this publication are likewise incorporated completely by reference. To carry out the fluidized-bed drying process, it is advantageous that the carrier material to be used, in particular the matrix component, is introduced in a fluidized bed and this is sprayed with the microorganism suspension in the manner described by U. Kessler.

However, the drying process which is most preferred according to the invention is spray-drying. Those methods which can be used according to the invention are essentially all spray-drying techniques known hitherto. The material to be sprayed can, for example, be dried cocurrently or countercurrently; spraying can be carried out by means of a single-component or multiple-component nozzle or by means of an atomizer wheel.

Preference is given according to the invention to the use of material to be sprayed having a solids content (after addition of the carrier) of from about 10 to 40, such as from about 10 to 25% by weight.

The spray-drying process according to the invention is carried out in such a manner that a conditioned dry gas having a temperature in the range of above about 80° C. is introduced into the drying apparatus. In particular, the inlet temperature should be in the range of from about 90 to 135° C. Particular preference is given to a drying temperature in the range of about 105° C. The rate of the drying process is designed according to the invention in such a manner that the exit temperature of the drying material from the dryer is in the range of about 45 to 75° C., in particular in the range of from about 50 to 65° C., preferably about 55° C.

Of particular importance to the process according to the invention is the use of preconditioned, i.e. low-moisture, drying air. Preferably, use is made of compressed air having a dew point at about −25° C.

The drying process according to the invention shall be carried out in such a manner that a very low residual moisture content is present in the dry material. Preferably, the water activity $a_w$ in the drying material should be less than 0.4. However, to further improve the long-term storage stability, according to the invention water activities of less than 0.15, preferably in the range from about 0.03 to 0.1 are sought after. The percentage water content is preferably from about 2 to 3% by weight. Most preferably, this is achieved by adding a post-drying step subsequently to the spray-drying step. The drying material for this purpose is, for example, post-dried in a fluidized bed, preferably at a temperature in the range of from 15 to 50° C., for a period of, for example, from 15 minutes to 20 hours. Again, preferably, conditioned compressed air or conditioned nitrogen serves as drying gas. However, the post-drying can also be performed by applying a vacuum of from about 1 to 50 mm Hg for a period of from about 15 minutes to 20 hours and at a temperature of from about 15 to 50° C. In this case, preference is given to stirring the drying material, for example, using a paddle agitator.

Instead of the above-described physical post-drying processes, it is also conceivable to add specific desiccants to the dry material obtained from the spray-drying. Desiccants of this type should themselves have a very low water activity, such as an $a_w$ of 0.01 or less. Examples of suitable desiccants are inorganic salts, such as calcium chloride and sodium carbonate, organic polymers, such as the product obtainable under the trade name Kollidon 90 F, and silicon-dioxide-containing desiccants, such as silica gel, zeolites and desiccants which are obtainable under the trade name Tixosil 38, Sipernat 22 S or Aerosil 200.

According to the invention, it was surprisingly found that, despite the relatively high drying temperatures, the survival rate for the dry preparations according to the invention had excellent values, namely of 75%±25%.

The content of viable microorganisms is in the range of from about $5\times10^8$ to $1\times10^{12}$ cfu/g of dry matter. These preparations are also called according to the invention powder concentrates. Since, for individual final applications, lower contents of viable microorganisms are also completely sufficient, powder concentrates of this type can therefore if appropriate be blended to the final count of viable microorganisms by mixing with further inert carrier material.

Preparation of Compressed Dry Microorganism Cultures

The powder concentrates obtainable by the above-described drying processes usually have a relatively high dust content and are thus not yet satisfactorily handleable for individual applications. Furthermore, various applications require an increased mechanical stability of the dry cultures. It is therefore necessary to improve the properties of the above-described powder concentrates by a further compression step.

To reduce the dust content of the powder concentrates according to the invention, it is possible to agglomerate these in a conventional manner to form granules, or using external forces, to compact them or tablet them.

Agglomeration is a generally known process, and is described, for example, by Schade, A. and Leuenberger, H. in Continuous fluidized-bed spray granulation, Chemie Ingenieur Technik (1992) 64 (1992) 1016; Uhlemann, H., Preparation of pharmaceutical granules in a combined wet granulation and multichamber fluidized-bed drying process, Chemie Ingenieur Technik 62 (1990), 822; or Rosch, M. and Probst R., Granulation in the fluidized bed, Verfahrenstechnik (1975), 9, 59.

Use can be made according to the invention of agglomeration using a mixer. For this purpose, the above-described powder concentrate is charged into the mixer and oil, water or an aqueous or alcoholic solution of sugars, polymers or other additives is sprayed in to agglomerate the powder concentrate.

In addition, use can be made according to the invention of agglomeration in a fluidized bed. In this case, powder concentrate is vortexed with gas feed and sprayed with an aqueous or alcoholic solution of sugars, polymers or other additives to form the agglomerate. Suitable processes for this purpose are described, for example, in WO-A-88/06181, in the dissertation by U. Kessler (loc. cit.) and by K. Fuchs in ZFL 45 (1994) 31. The disclosure of the abovementioned publications is hereby incorporated by reference.

Agglomeration produces granulated microorganism cultures having a particle size in the range of from about 0.1 to about 4 mm, in particular from about 0.3 to 2.5 mm.

However, particularly preferred according to the invention is the preparation of dry microorganism cultures which are present in the form of particularly highly compressed particles. This is carried out according to the invention either by tabletting in conventional tablet presses or with the use of conventional compacting apparatuses equipped with two counter-rotating rolls.

To compress the powder concentrates obtainable according to the invention, to these are usually added one or more coformulants or additives to modify the processability to the end product or the properties of the end product.

To improve the flowability of the powder concentrate, a free-flowing agent is preferably added. Examples of a suitable free-flowing agent are spray-dried silicon dioxide powders, which are obtainable, for example, under the trade name Sipernat 50. To improve the storage stability of the solid formulations according to the invention, in addition, conventional antioxidants, such as L-ascorbic acid, can be added. Furthermore, desiccants of the above-described type can additionally be added.

The action of the cultures according to the invention is markedly improved if measures are taken which, after the culture has been applied, lead to a rapid breakdown of the grain structure and thus to a rapid release of the microorganisms. One possibility of achieving this is the addition of a readily water-soluble component which thus accelerates the breakdown of the grain structure. Suitable compounds are, for example, poly(ethylene glycol)s, which are obtainable, for example, under the trade name Pluriol E.

Another solid formulation particularly preferred according to the invention comprises what is termed an effervescence additive. This is a gas-releasing component, in particular a $CO_2$ source, for example an alkaline earth metal hydrogen carbonate, preferably sodium hydrogen carbonate or ammonium hydrogen carbonate; and an acid component, preferably selected from citric acid, ascorbic acid or malic acid. This effervescence additive, in the presence of moisture, produces a spontaneous gas formation with breakdown of the grain structure and rapid release of the microbial cells.

In particular, to prepare highly compressed, compacted or tabletted microorganism cultures, it is advisable to add compacting or tabletting aids. This is because it has surprisingly been found according to the invention that adding such compacting aids decreases the pressures acting on the microorganisms during the compacting and thus markedly improves the survival rate of the microbes. Examples of suitable compacting aids are microcrystalline cellulose, sugars and mixtures thereof. Concrete examples of microcrystalline cellulose are products which are commercially available under the trade names Avicel, Arbocel and Vivapur. Examples of suitable sugars are maltose, maltodextrin and lactose preparations, which are obtainable under the trade names Granulac, Tablettose or FloLac. An example of a suitable mixed cellulose/sugar product is the commercial preparation Cellactose. A further suitable tabletting aid is a lactose preparation granulated using PVP, obtainable under the trade name Ludipreβ.

Other suitable additives are poly(ethylene glycol)s (Mw from 100 to 10,000) which can have a stabilizing action on the cells embedded in the matrix.

The accompanying FIG. 1 shows a flow diagram for the further processing according to the invention of the powder concentrates to give a compacted product according to the invention. Powder concentrate PK is mixed in the mixer M1 with the coformulants or additives ZU, passes from there into a reservoir B1 which feeds the compactor A1. The product ribbon exiting from the compactor is precomminuted or finely comminuted in the grinders Z1 and Z2 and in the screen F1, product PR is separated off from dust fractions having a particle size of less than 0.3 mm. This material is fed to the mixer M1 as recycled material RÜ. The product PR having a particle size of 0.3 mm or above, such as from 0.3 to 1.5 mm, passes to the packaging station or may be subjected to further processing, such as a coating process.

Suitable coating materials, which preferably are additionally to hinder the ingress of moisture to the dry preparation, are, for example, alcoholic solutions of PVP, in particular a PVP product which is commercially available under the trade name Kollidon VA64. Another usable coating system is a mixture of shellac and Kollidon 25 or 30, which is supplemented with titanium dioxide and tallow and is likewise present in alcoholic solution.

To reduce the cell count further if necessary, a coated or uncoated product obtained in this manner can be blended, for example, with lime, or another suitable mineral additive.

EXAMPLES

Analytical Methods Used in the Following Examples a) Cell Count Determination:

Cell counts are determined in the conventional manner by serial dilution with sterile 0.9% strength NaCl solution and subsequent plating on MRS agar (Difco Laboratories). Colony-forming units (cfu) were counted after incubation for 48 hours at 37° C. Only plates which contained between 30 and at most 300 colonies were evaluated. Generally, 3 plates per stage were evaluated and the mean taken.

The specific cell count of a sample was determined by calculation, dividing the cell count per gram of sample by the relative sample dry matter content.

b) Determination of the Survival Rate on Drying:

The survival rate during drying was calculated from the specific cell count of the sample before drying divided by the specific cell count after drying. It was always expressed in percent.

c) Determination of Storage Stability:

To determine the storage stability of a dried sample, the specific cell count of the dried sample was determined immediately after drying ($day_O$). The dried cell material was stored under air in an opaque tightly sealed vessel at room temperature (21° C.±2° C.) for extended periods. The specific cell count was determined again at regular intervals ($day_N$). The storage stability was calculated from the quotient of specific cell count $day_N$/specific cell count $day_O$.

If the specific cell count after drying was, for example, $5 \cdot 10^{11}$ cfu/g of DM and, after storage for 8 weeks, $4 \cdot 10^{11}$ cfu/g of DM, the storage stability was 80% of the initial value.

d) Moisture Content Measurement:

Electronic moisture analyzer HR 73 from Mettler Procedure: approximately 2 g of powder are distributed onto the measuring scales of the instrument. Measurements are taken at a drying temperature of 105° C. up to constant weight (switch-off criterion: max. 1 mg of weight loss in 50 seconds).

e) Measurement of Water Activity:

Hygroscope DT instrument from Rotronic AG, Zürich, Switzerland The product is placed in the sample holder and this is positioned in the measuring chamber thermostatted to 25° C. After closing the measuring chamber and an equilibration time of 20 minutes, the instrument measurement value is read off.

f) DSC Measurement to Determine the Glass Transition Temperature $T_g$:

TA4000 instrument from Mettler Sample weight approximately 15 mg, heating rate 20° C./min, samples were flushed with a nitrogen stream during measurement.

DSC=Differential Scanning Calorimetry

Microorganism Culture Examples

Example K1

Batch Fermentation 10 Liter Scale 10 l of a fermentation medium which comprised the following constituents were placed in a 14 l fermenter and sterilized at 121° C. for 30 minutes:

| | |
|---|---|
| Glucose monohydrate | 550.0 g |
| 50% yeast extract suspension (pH 4.5 with phosphoric acid) | 750.0 g |
| Tween 80 ® | 10.0 g |
| MgSO$_4$ * 7 H$_2$O | 5.0 g |
| MnSO$_4$ * 1 H$_2$O | 0.5 g |

After sterilization, the medium was adjusted to pH 5.8 at 37° C. using sterile 25% strength sodium hydroxide solution and the medium was blanketed with a gentle stream of sterile nitrogen. The fermenter was stirred at 150 rpm.

The fermenter was then inoculated with 100 ml of a preculture of Lactobacillus plantarum (BASF strain LU 3244) which had previously been grown for 16 h at 37° C. in MRS nutrient medium (Difco Laboratories). The culture pH was continuously kept at 6.2 using 25% strength sodium hydroxide solution.

The course of the fermentation was followed from the sodium hydroxide solution consumption. As soon as no more sodium hydroxide solution was consumed (total consumption 890 g), all of the fermentation broth was drained off and centrifuged at 8° C. The biomass was resuspended in about 600 g of supernatant and made up to exactly 1000 g with supernatant. The dry matter content was determined using an infrared drying balance (105° C. to constant weight). The solids content of this suspension was 15%.

Example K2

Batch Fermentation 200 Liter Scale 180l of a fermentation medium which comprised the following constituents were placed in a 200 l fermenter and sterilized at 121° C. for 30 minutes:

| | |
|---|---|
| Glucose monohydrate | 11 kg |
| 50% yeast extract suspension | 15 kg |
| Tween 80 ® | 200 g |
| MgSO$_4$ * 7 H$_2$O | 200 g |
| MnSO$_4$ * 1 H$_2$O | 10 g |

After sterilization, the medium was adjusted to pH 5.8 at 37° C. using sterile 25% strength sodium hydroxide solution and the medium was blanketed with a gentle stream of sterile nitrogen.

The fermenter was then inoculated with 2000 ml of a preculture of Lactobacillus plantarum (3244) which had previously been grown for 24 h at 30° C. in MRS nutrient medium. The pH of the culture was continuously controlled using 25% strength sodium hydroxide solution.

The course of the fermentation was followed from the sodium hydroxide solution consumption. In total, 16.43 kg of 25% strength NaOH were consumed. As soon as sodium hydroxide solution was no longer consumed, all of the fermentation broth was drained off and harvested at 8° C. using a continuous separator. The harvested biomass had a weight after centrifugation of 20 kg, and the solids content of this suspension was 12.3%. The cell count of the suspension was $1.04 \cdot 10^{11}$ cfu/g of suspension. The specific cell count was $8.45 \cdot 10^{11}$ cfu/g of dry matter (DM).

Example K3

Batch Fermentation With Temperature Shock

A fermentation was carried out in a similar manner to Example 2. At a sodium hydroxide consumption corresponding to 90% of the expected value, the fermenter temperature was increased to 44° C. and kept until all of the sugar present had been consumed. The cells were then harvested as described in Example K2. The cell count of the fermentation broth was $1.8 \cdot 10^{11}$ cfu/g at a solids content of 21.17%. This corresponds to a specific cell count of $8.5 \cdot 10^{11}$ cfu/g DM.

Example K4

Continuous Fermentation 10 l of a fermentation medium having the following composition were charged into a 14 l fermenter and sterilized at 121° C. for 30 minutes (production fermenter):

| | |
|---|---|
| Glucose monohydrate | 400.0 g |
| 50% yeast extract suspension (pH 4.5 with phosphoric acid) | 500.0 g |
| KH$_2$PO$_4$ | 30.0 g |
| Citric acid monohydrate | 21.0 g |
| Tween 80 ® | 10.0 g |
| MgSO$_4$*7 H$_2$O | 5.0 g |
| MnSO$_4$*1 H$_2$O | 1.7 g |
| (NH$_4$)$_2$Fe(SO$_4$)$_2$* 6H$_2$O | 0.4 g |

2000 l of the same medium were charged into a second fermenter having a total volume of 3000 and sterilized (reservoir fermenter). Both fermenters were connected by a sterilizable line. Via an intermediate vessel which stood on a balance, using an automatic control system, 3 l of fresh medium were pumped every hour into the production fermenter. The temperature of the production fermenter was controlled to 37° C. The pH was controlled to 5.8 using 25% strength NaOH. The fermenter was stirred at 150 rpm and blanketed with nitrogen at 0.1 VVM.

Via a second pump, 3 l of medium were continuously taken off every hour and collected in a stainless steel collection vessel precooled to from 0 to 4° C. The biomass concentration was determined by turbidimetry and was 3.5 g/l. The glucose, concentration in the production fermenter effluent was, after the initial growth phase, 0 g/l at all times. The cell count of the fermentation broth was $1.48 \cdot 10^{10}$ cfu/g of broth. The dry matter content of the fermentation broth was 6.89%, equivalent to 217 g DM. The specific cell count was $2.15 \cdot 10^{11}$ cfu/g of DM.

Example K5

Cell Harvest With Washing Step to Remove Sodium Lactate 72 l of fermenter discharge from Example K4 were harvested continuously at 8° C. using a commercial separator. About 7 kg of cell suspension was obtained. To this was added a washing solution which comprised 40 l of deionized water, 450 g of NaCl and 136 g of $KH_2PO_4$. The pH of the washing solution had been adjusted in advance to 7.0 using 25% strength sodium hydroxide solution. The about 50 l of resuspended cells were again separated. 3160 g of concentrated washed cell suspension were obtained. The solids content of the suspension was 9.97%. The cell count was $2.49 \cdot 10^{11}$ cfu/g of suspension. The specific cell count was $2.5 \cdot 10^{12}$ cfu/g DM.

This washed cell suspension was virtually free of sodium lactate. The biomass concentration was determined by turbidimetry to be 80 g/l.

Examples of Preparation by Spray-Drying of Powder Concentrates According to the Invention The spray-drying experiments described in the following section for preparing powder concentrates according to the invention are carried out in a laboratory spray-dryer of type Niro Minor from Niro, Copenhagen, Denmark. The ready-to-spray bacterial suspension is sprayed via a two-component nozzle cocurrently with preconditioned heated compressed air into the plant drying tower, the dried product is separated from the air using a cyclone and collected.

Example S1

To prepare a coformulant solution, 200 ml of deionized water (completely demineralized water) are heated to 60° C. 150 g of sweet whey powder, 7.5 of NaCl, 3.8 g of $KH_2PO_4$, 3.8 g of citric acid and 3.8 g of L-ascorbic acid are dissolved therein, adjusted to pH 7 using 40% strength aqueous NaOH and made up to 400 g total mass using deionized water. This solution is cooled to 5° C.

200 ml of washed, i.e. essentially sodium-lactate-free centrifuged ferment (prepared in a similar manner to Example K5) (12.7% solids content (S.C.)) are placed in an ice bath at a temperature of 5° C. and 400 g of coformulant solution, cooled to 5° C., are added with stirring. The mixture of centrifuged ferment and coformulants is further stirred for 30 minutes at 500 rpm using a magnetic stirrer with ice bath cooling. By means of spray-drying (Niro Minor apparatus) the mixture is then converted into a powder concentrate A, which is separated off in the cyclone. In the course of this, the reservoir from which the mixture is metered is cooled to 4° C., the inlet temperature is from 105 to 110° C., the exit temperature is from 53.5 to 55.5° C. A two-component nozzle is used, conditioned air (dew point −25° C.) at 4 bar being used to spray the mixture of centrifuged ferment and coformulants.

The powder concentrate A is further dried at room temperature for 2 hours in a nitrogen-operated (dew point=−40° C.) fluidized bed, powder concentrate B being obtained.
Characterizations:
Ready-to-spray mixture: 35% S.C., $2.84 \cdot 10^{11}$ cfu/g of dry matter
Powder concentrate A: water activity $a_w=0.135$
Powder concentrate B: water activity $a_w=0.076$, moisture content 3.4%,
$T_g$ from DSC measurement: 54° C.,
$1.98 \cdot 10^{11}$ cfu/g of dry matter (equivalent to 70% survival rate in the drying)
Storage study of powder concentrate B: cfu counts with room-temperature storage in containers sealed under ambient air: $2.0 \cdot 10^{11}$ cfu/g of dry matter (100%) after 30 days

Example S2

To prepare a coformulant solution, 200 ml of deionized water are heated to 70° C. 75 g of maltodextrin (Glucidex IT6, Roquette), 75 g of lactose, 7.5 g of NaCl, 3.8 g of $KH_2PO_4$, 3.8 g of citric acid and 3.8 g of L-ascorbic acid are dissolved therein, the mixture is adjusted to pH 7 using 40% strength aqueous NaOH and made up to 400 g total mass using deionized water. This solution is cooled to 5° C.

200 ml of washed, i.e. essentially sodium-lactate-free centrifuged ferment (16.5% S.C.; prepared similarly to example K5) are mixed, at 5° C., with stirring into 400 g of coformulant solution, cooled to 5° C. The mixture is stirred for 30 minutes at 250 rpm by a magnetic stirrer with ice bath cooling. 101 ml of a solubilized mixture prepared in accordance with EP-A-0 479 066 (BASF) from 25% Tween 80, 5% β-carotene and 2% α-tocopherol are then added and further stirred for 10 minutes with ice bath cooling. This mixture is then converted by spray-drying, as described in Example S1, into a powder concentrate A (inlet temperature 105° C., exit temperature from 54 to 55° C.). The powder concentrate A is not further dried.
Characterizations:
Ready-to-spray mixture: 29% S.C., $3.84 \cdot 10^{11}$ cfu/g of dry matter
Powder concentrate A: water activity $a_w=0.065$, moisture content 2.8%,
$T_g$ from DSC measurement: 61° C.,
$2.22 \cdot 10^{11}$ cfu/g of dry matter (equivalent to 58% survival rate in the drying)
Storage Study on Powder
concentrate A: cfu counts for room-temperature storage in containers sealed under ambient air:
$1.9 \cdot 10^{11}$ cfu/g of dry matter (86%) after 30 days

Example S3

400 ml of unwashed, i.e. sodium-lactate-containing, centrifuged ferment (prepared similarly to Example K4)(14.3% S.C.) are placed in an ice bath at a temperature of 5° C. 57.2 g of Glucidex IT6, 8.6 g of L-ascorbic acid and 5.7% of sodium glutamate are stirred as solids into the cooled centrifuged ferment with stirring at 700 rpm by means of a magnetic stirrer. The pH is adjusted to 7 using 40% strength aqueous NaOH. The mixture of centrifuged ferment and coformulants is further stirred for 30 minutes at 500 rpm using a magnetic stirrer at approximately 3° C. with ice bath cooling. The mixture is then converted by spray-drying, as described in Example S1, into a powder concentrate A (inlet temperature 105° C.; exit temperature from 54.5 to 55.5° C.).

The powder concentrate A is further dried at room temperature in a nitrogen-operated fluidized bed for 2 hours, a powder concentrate B being obtained.
Characterizations:
Ready-to-spray mixture: 27% S.C., $4.65 \cdot 10^{11}$ cfu/g of dry matter
Powder concentrate A: water activity $a_w=0.197$
Powder concentrate B: water activity $a_w=0.072$, moisture content 3.8%, $T_g$ from DSC measurement: 52° C.,
4.64·10$^{11}$ cfu/g of dry matter (equivalent to 100% survival rate in the drying)

Storage Study on Powder Concentrate B:
cfu counts with room-temperature storage in containers sealed under ambient air:
4.1·10$^{11}$ cfu/g of dry matter (88%) after 28 days Example S4

215 ml of washed, i.e. essentially sodium-lactate-free, centrifuged ferment (prepared similarly to Example K5) (14.5% S.C.) are placed in an ice bath at a temperature of 5° C. 31.2 g of Glucidex IT6, 4.7 g of ascorbic acid and 3.1% of sodium glutamate are then stirred in as solids into the cooled centrifuged ferment with stirring at 700 rpm by a magnetic stirrer. The pH is adjusted to 7 using 40% strength aqueous NaOH. The mixture of centrifuged ferment and coformulants is further stirred for 30 minutes at 500 rpm using a magnetic stirrer with ice bath cooling. The mixture is then converted by spray-drying, as described in Example S1, into a powder concentrate A (inlet temperature 105° C.; exit temperature from 54.5 to 55.5° C.).

The powder concentrate is further dried at room temperature in a nitrogen-operated fluidized bed for 2 hours, powder concentrate B being obtained.

Characterizations:
Ready-to-spray mixture: 28% S.C., 8.76·10$^{11}$ cfu/g of dry matter
Powder concentrate B: water activity $a_w$=0.044, moisture content 3.8%,
$T_g$ from DSC measurement: 48° C.,
7.17·10$^{11}$ cfu/g of dry matter (equivalent to 82% survival rate in the drying)

Storage Study on Powder
concentrate B: cfu counts for room-temperature storage in containers sealed under ambient air:
3.7·10$^{11}$ cfu/g of dry matter (52%) after 27 days Example S5

To prepare a coformulant solution 1, 40 ml of deionized water are charged and 33.3 g of lactose and 6.3 g of peptone are dissolved therein, the mixture is made up to a total mass of 83 g with deionized water and adjusted to pH 7 using 40% strength aqueous NaOH. To prepare a coformulant solution 2, 40 ml of deionized water are charged and 33.3 g of glucose-1-hydrate and 5.4 g of citric acid are dissolved therein, the mixture is made up to a total mass of 83 g with deionized water and adjusted to pH 7 using 40% strength aqueous NaOH. These solutions 1 and 2 are cooled to 5° C.

200 ml of washed, i.e. essentially sodium-lactate-free, centrifuged ferment (prepared similarly to Example K5) (12.7% S.C.) are mixed with 83 g of the cooled coformulant solution 1 in an ice bath at approximately 4° C. The mixture is stirred for 30 minutes with ice bath cooling. 83 g of the cooled coformulant solution 2 are then added with stirring and further stirred for 30 minutes with ice bath cooling. Then this mixture is converted by spray-drying, as described in Example S1, into a powder concentrate A (inlet temperature 105° C.; exit temperature 55° C.).

The powder concentrate A is further dried at room temperature for 2 hours in a nitrogen-operated fluidized bed, powder concentrate B being obtained.

Characterizations:
Ready-to-spray mixture: 29% S.C., 7.30·10$^{11}$ cfu/g of dry matter Powder concentrate B: water activity $a_w$=0.139, moisture content 3.7%,
$T_g$ from DSC measurement: 45° C.,
5.06·10$^{11}$ cfu/g of dry matter (equivalent to 69% survival rate in the drying)

Storage Study on Powder
concentrate B: cfu counts at room-temperature storage in containers sealed under ambient air:
4.8·10$^{11}$ cfu/g of dry matter (95%) after 21 days Example S6

The ready-to-spray mixtures were prepared in a similar manner to Example S3. Here, however, two different centrifuged ferments were used:

Example S6a: batch fermentation, with the ferment having been cooled to 4° C. for 40 minutes toward the end of the fermentation.

The powder concentrate A obtained in the spray-drying in accordance with Example S1 (inlet temperature from 107 to 111° C.; exit temperature from 58 to 61° C.) was not further dried.

Characterizations:
Ready-to-spray mixture: 3.68·10$^{11}$ cfu/g of dry matter
Powder concentrate A: 0.76·10$^{11}$ cfu/g of dry matter (equivalent to 21% survival rate in the drying)

Example S6b: batch fermentation, with the ferment having been heated to 44° C. toward the end of the fermentation. In this example, the ready-to-spray mixture was divided. In a first experiment, the reservoir vessel was thermostatted to 4° C., as in Examples S1 to S5 and S6a. In a second experiment, the reservoir vessel was thermostatted to 20° C.

The powder concentrates A obtained by spray drying in accordance with Example S1 (inlet temperature from 103 to 110° C.; exit temperature from 59 to 61° C.) were not post-dried.

Characterizations for Rreservoir at 4° C.:
Ready-to-spray mixture: 3.53·10$^{11}$ cfu/g of dry matter
Powder concentrate A: 2.36·10$^{11}$ cfu/g of dry matter (equivalent to 67% survival rate in the drying)

Characterizations for Reservoir at 20° C.:
Ready-to-spray mixtures:3.53·10$^{11}$ cfu/g of dry matter
Powder concentrate A: 1.48·10$^{11}$ cfu/g of dry matter (equivalent to 42% survival rate in the drying)

Formulation Examples

In accordance with the formulas stated below, dry mixtures of powder concentrates according to the invention were prepared and processed to form compacted starter culture preparations:

Unless specified otherwise, the release agent used was Leucine and the free-flowing agent used was Sipernat 50S (spray-dried silicon dioxide).

The individual components of the preparations are first mixed with one another. For this purpose, for example, a plowshare mixer is used (type Lö 20 from Lödige). The dry mixture obtained in this manner is compacted in a compactor. For example, for this purpose a laboratory compactor can be used which applies a pressing force of 14 kN/cm$^2$ (e.g. laboratory compactor L 200 from Bepex). The product ribbon exiting from the compactor is then comminuted to a particle size of≦1.25 mm. The crude granules are screened to separate off fines of a particle size of≦0.3 mm. The yield of useful material is about from 50 to 60% of the material used.

Example F1

Preparing a Compacted Effervescent Product for Use as Starter Culture for Silage

| Preparation A: | |
|---|---|
| Powder concentrate (in accordance with Example S2) | 200.0 g |
| Citric acid, anhydrous | 95.0 g |
| NaHCO$_3$ | 95.0 g |
| PEG (M$_w$ < 400) | 8.0 g |
| Free-flowing agent | 2.0 g |
| Preparation B: | |
| Powder concentrate (according to Example S2) | 100.0 g |
| Ascorbic acid, powder | 47.5 g |
| NaHCO$_3$ | 47.5 g |
| PEG (M$_w$ < 400) | 4.0 g |
| Free-flowing agent | 1.0 g |
| Preparation C: | |
| Powder concentrate (according to Example S2) | 100.0 g |
| Malic acid | 47.5 g |
| NaHCO$_3$ | 47.5 g |
| PEG (M$_w$ < 400) | 4.0 g |
| Free-flowing agent | 1.0 g |
| Preparation D: | |
| Powder concentrate (in accordance with Example S2) | 100.0 g |
| Zeolite A (Wessalith P) | 20.0 g |
| Ascorbic acid, powder | 37.0 g |
| NaHCO$_3$ | 36.8 g |
| Release agent | 3.0 g |
| Free-flowing agent | 3.0 g |

Example F2

Preparation of a Quick-Dissolving Compacted Mixture Without Effervescent Additive

| | |
|---|---|
| Powder concentrate (according to Example S2) | 100.0 g |
| water-soluble surfactant (Pluriol EL 500) | 90.0 g |
| Release agent | 7.0 g |
| Free-flowing agent | 3.0 g |

Example F3

Preparation of a Compacted Mixture

| | |
|---|---|
| Powder concentrate (in accordance with Example S5) | 100.0 g |
| Compacting aid[1] | 90.0 g |
| Release agent | 7.0 g |
| Free-flowing agent | 3.0 g |

[1] selected from: Avicel PH 102, Vivapur 105, FlowLac, Maltex 20, Cellactose or mixtures thereof

Example F4

Preparation of Stabilized Compacted Mixtures

Base Formula:

| | |
|---|---|
| Powder concentrate (according to Example S5) | 100.0 g |
| Compacting aid | 50.0 g |
| Stabilizer | cf. Table I |
| Release agent | 7.0 g |
| Free-flowing agent | 3.0 g |

TABLE I

| Stabilizer | Component | Amount (g) |
|---|---|---|
| A | Zeolite A | 40 |
| B | PEG 4000 | 40 |
| C | Ascorbic acid[1] | 40 |
| D | PEG 4000 | 20 |
| | Ascorbic acid | 20 |
| E | Zeolite A | 20 |
| | Ascorbic acid | 20 |
| F | Zeolite A | 20 |
| | Ascorbic acid | 3 |
| | PEG 4000 | 17 |
| G | Zeolite A | 10 |
| | Ascorbic acid | 1.5 |
| | PEG 4000 | 8.5 |
| H | Zeolite A | 7 |
| | Ascorbic acid | 1 |
| | PEG 4000 | 6 |

[1] in each case L-ascorbic acid

We claim:

1. A dry microorganism culture which comprises at least one microorganism species in carrier-bound form, wherein the culture is present in the form of particles which
   a) have a particle size of at least about 0.1 mm and
   b) comprise from about $10^{10}$ to $10^{12}$ cfu/g of at least one microorganism species;
   c) have a water activity $a_w$ of less than 0.15: and
   d) are compressed.

2. A microorganism culture as claimed in claim 1, wherein the particles have been compressed under the action of a linear force from about 5 to 15 kN/cm or a pressure from about 90 to 160 MPa.

3. A microorganism culture as claimed in claim 1, wherein the compressed particles comprise compacted broken material having a diameter of from about 0.1 mm to about 2 mm.

4. A microorganism culture as claimed in claim 1, wherein the compressed particles comprise tablets having a diameter of from about 2 to 50 mm and a ratio of diameter to thickness of from about 1:0.1 to about 10:1.

5. A microorganism culture as claimed in claim 1, wherein it comprises, a further component, an effervescent additive.

6. A microorganism culture as claimed in claim 1, wherein, as carrier, it comprises at least one matrix material for embedding the microorganism cells with or without at least one further cell-stabilizing additive.

7. A microorganism culture as claimed in claim 1, wherein it comprises at least one lactic-acid-producing bacterial species.

8. A microorganism culture as claimed in claim 7, wherein the bacterial species is selected from bacteria of the genus Lactobacillus sp.

9. A process for producing a dry microorganism culture, comprising at least one microorganism species in carrier-bound form and having a water activity $a_w$ of less than 0.15, which process comprises,
   a) dissolving or suspending at least one substance suitable for forming a carrier in a liquid comprising at least one microorganism species,
   b) drying the resultant mixture in a spray-dryer, for the spray-drying use being made of a conditioned dried gas having a dew point of less than about +5° C., heated to a temperature in the range of above about 80° C., and c) removing the dried material from the spray dryer, this dried material having an exit temperature of from about 45 to 75° C.

10. A process as claimed in claim 9, wherein, in a further stage d), the dry material is subjected to a further drying at a temperature in the range from about 15 to 50° C. in a gas atmosphere or in vacuo and/or at least one desiccant is added.

11. A process as claimed in claim 9, wherein, as dry material, a powder concentrate having a content of viable microorganisms of from about $5 \cdot 10^8$ to $1 \cdot 10^{12}$ cfu/g is obtained.

12. Dry compressed microorganism culture according to claim 1, obtained from a powder concentrate of microorganism culture dried in a spray-dryer, for the spray-drying use being made of a conditioned dried gas having a dew point of less than about +5° C., heated to a temperature in the range of above about 80° C.

13. A process for preparing a dry microorganism culture as claimed in claim 1, which comprises i) producing a powder concentrate of the microorganism culture by carrier-bound spray-drying, carrier-bound freeze-drying or carrier bound fluidized-bed drying, ii) with or without admixing the powder concentrate with one or more coformulants and iii compacting or tableting this mixture.

14. A process as claimed in claim 13, wherein the compacted powder concentrate from stage iii) is broken, with or without classification.

15. A process for preparing a dry agglomerated microorganism culture, which comprises i) preparing a powder concentrate of the microorganism culture by carrier-bound spray-drying, carrier bound freeze drying or carrier-bound fluidized-bed drying which powder concentrate has a water activity $a_w$ of less than 0.15, ii) with or without admixing the powder concentrate with one or more coformulants and iii) agglomerating this mixture.

16. A process as claimed in claim 13, wherein the spray-drying is performed in a spray-dryer in which a conditioned dried gas is employed having a dew point of less than about +5° C., heated to a temperature in the range of above about 80° C.

17. A starter culture for foodstuffs and feedstuffs comprising a microorganism culture as claimed in claim 1, or prepared by a process for producing a dry microorganism culture, comprising at least one microorganism species in carrier-bound form, which comprises a) dissolving or suspending at least one substance suitable for forming a carrier in a liquid comprising at least one microorganism species, b) drying the resultant mixture in a spray-dryer, for the spray-drying use being made of a conditioned dried gas having a dew point of less than about +5° C., heated to a temperature in the range of above about 80° C., and c) removing the dried material from the spray dryer, this dried material having an exit temperature of from about 45 to 75° C.

18. A foodstuff or feedstuff obtainable by using a microorganism culture as claimed in claim 1 or prepared by a process for producing a dry microorganism culture, comprising at least one microorganism species in carrier-bound form, which comprises a) dissolving or suspending at least one substance suitable for forming a carrier in a liquid comprising at least one microorganism species, b) drying the resultant mixture in a spray-dryer, for the spray-dryer use being made of a conditioned dried gas having a dew point of less than about +5° C., heated to a temperature in the range of above about 80° C., and c) removing the dried material from the spray-dryer, this dried material having an exit temperature of from about 45 to 75° C.

19. A process as claimed in claim 15, wherein the spray-drying is performed in a spray-dryer employing a conditioned dried gas having a dew point of less than about +5° C., heated to a temperature in the range of above about 80° C.

20. A powder concentrate of a microorganism culture comprising from about $4 \times 10^{11}$ to $10^{12}$ cfu/g of at least one microorganism species and having a water activity $a_w$ of less than 0.15.

* * * * *